US007072710B2

(12) United States Patent
Chamney

(10) Patent No.: US 7,072,710 B2
(45) Date of Patent: Jul. 4, 2006

(54) METHOD AND A DEVICE FOR DETERMINING THE DRY WEIGHT OF A PATIENT WITH KIDNEY FAILURE

(75) Inventor: Paul Chamney, Herts (GB)

(73) Assignee: Fresenius Medical Care Deutschland GmbH, Bad Homburg (DE)

(*) Notice: Subject to any disclaimer, the term of this patent is extended or adjusted under 35 U.S.C. 154(b) by 416 days.

(21) Appl. No.: 10/415,646

(22) PCT Filed: Nov. 6, 2001

(86) PCT No.: PCT/EP01/12829

§ 371 (c)(1),
(2), (4) Date: Nov. 7, 2003

(87) PCT Pub. No.: WO02/36004

PCT Pub. Date: May 10, 2002

(65) Prior Publication Data

US 2004/0064063 A1  Apr. 1, 2004

(30) Foreign Application Priority Data

Nov. 6, 2000 (EP) .................................. 00124111

(51) Int. Cl.
*A61B 5/05* (2006.01)
(52) U.S. Cl. ........................................ 600/547; 604/29
(58) Field of Classification Search ............... 600/300, 600/322–327, 485, 490, 500, 504–506, 531–538, 600/547; 210/646–647; 604/29, 66–67
See application file for complete search history.

(56) References Cited

U.S. PATENT DOCUMENTS

| 4,008,712 | A | | 2/1977 | Nyboer ................... 128/2.1 Z |
| 5,086,781 | A | | 2/1992 | Bookspan ................... 128/734 |
| 5,449,000 | A | * | 9/1995 | Libke et al. ................ 600/547 |
| 5,788,643 | A | * | 8/1998 | Feldman ..................... 600/506 |
| 6,246,894 | B1 | * | 6/2001 | Steuer et al. ............... 600/322 |
| 6,615,077 | B1 | * | 9/2003 | Zhu et al. ................... 600/547 |

FOREIGN PATENT DOCUMENTS

| EP | 0 865 763 | 9/1998 |
| JP | 09-220209 | 8/1997 |
| WO | 92/19153 | 11/1992 |

OTHER PUBLICATIONS

Zhu et al., Validation of Changes in Extracellular Volume Measured During Hemodialysis Using a Segmental Biompedance Technique, 1998, ASAIO Journal, vol. 4535, pp. M541-545.*

* cited by examiner

*Primary Examiner*—Max Hindenburg
*Assistant Examiner*—Rene Towa
(74) *Attorney, Agent, or Firm*—Jacobson Holman PLLC

(57) ABSTRACT

A system and method for determining the dry weight $wgt_{dry}(t)$ of a patient at a time t by determining the extracellular water volume ECV(t) and the weight Wgt(t) of the patient at time t and by deriving the dry weight $wgt_{dry}(t)$ of the patient from an intersection of a function derived from the determined ECV(t) and Wgt(t) values with a previously established extracellular water volume (ECV) against dry weight ($wgt_{dry}(t)$) reference relation representing healthy subjects. To obtain more accurate results it is also proposed to take into account a compartmental mass correction $\Delta m(t)$. The invention also relates to a device for deriving the dry weight $wgt_{dry}(t)$.

25 Claims, 8 Drawing Sheets

Figure 1:
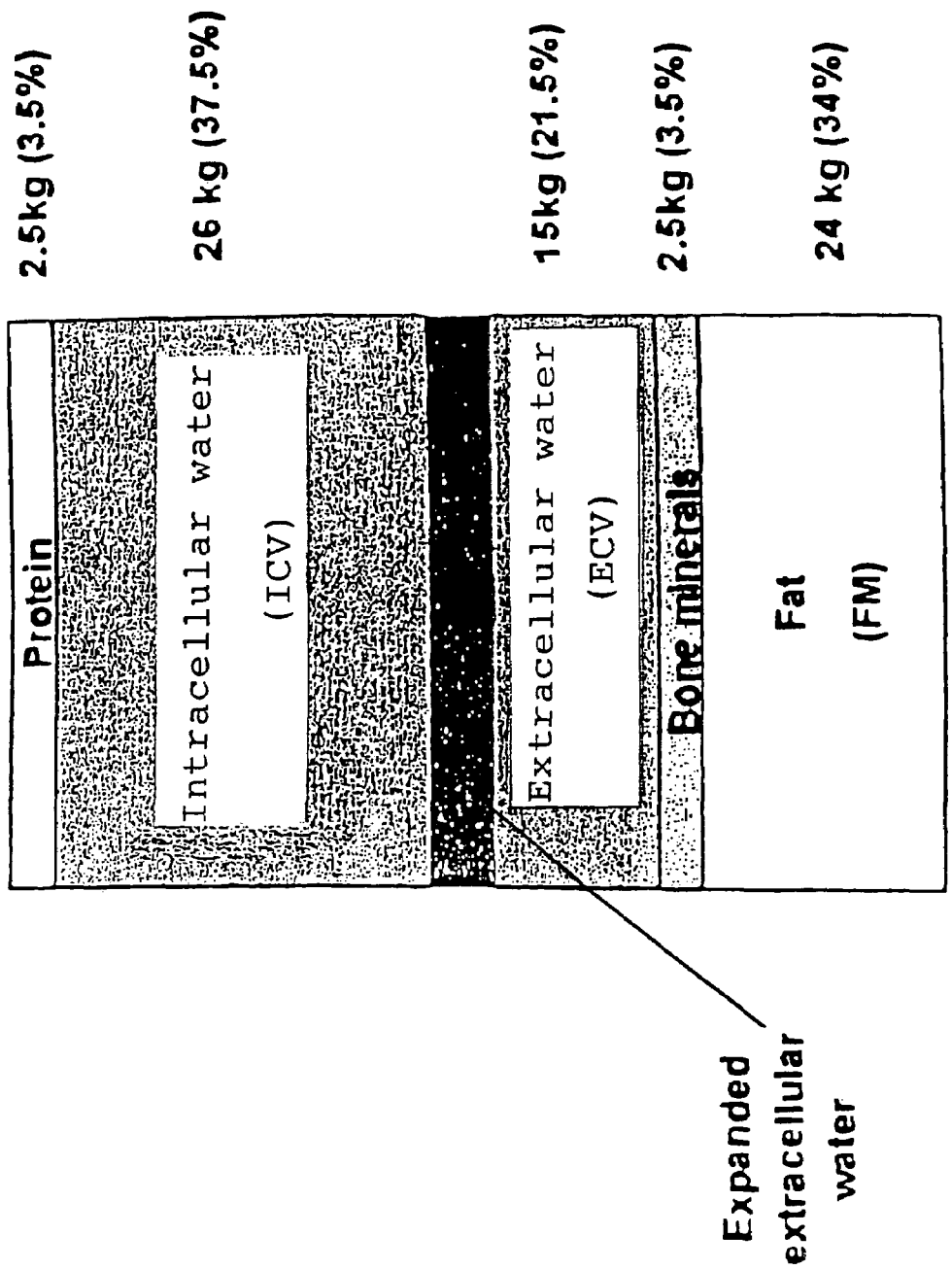

METHOD AND A DEVICE FOR DETERMINING THE DRY WEIGHT OF A PATIENT WITH KIDNEY FAILURE

This is a nationalization of PCT/EP01/12829, filed Nov. 6, 2001 and published in English.

The invention relates to a method and a device for monitoring the fluid status of a patient according to the preamble of claims 1 and 12, respectively.

The kidneys carry out several functions for maintaining the health of a human body. First, they control the fluid balance by separating any excess fluid from the patient's blood volume. Second, they serve to purify the blood from any waste substances like urea or creatinine. Last not least they also control the levels of certain substances in the blood like electrolytes in order to ensure a healthy and necessary concentration level.

In case of renal failure all forms of ingested fluid accumulate in body tissues causing increased stress on the circulatory system. This surplus fluid has to be removed during a dialysis treatment by ultrafiltration of the blood. If insufficient fluid is removed the long term consequenses can be severe, leading to high blood pressure and cardiac failure. Cardiac failure itself is many times more likely to occur in dialysis patients and it is thought that states of fluid overload are one of the major contributing factors. Removal of too much fluid is also dangerous since the dialysis patient becomes dehydrated and this invariably leads to hypotension.

The dry weight defines the weight of a patient that would be achieved if the kidneys were working normally. In other words this represents the optimal target weight (or fluid status) which should be achieved in order to minimise cardiovascular risk. Dry weight has always been an elusive problem in routine clinical practise due to lack of quantitative methods for its assessment. Currently the dry weight problem is approached using indirect indicators e.g. blood pressure, echocardiographic investigations and subjective information such as X-rays. Furthermore it has been particularly difficult to define a set of conditions which are universally accepted as the dry weight standard.

A promising method to derive the fluid status of a patient involves the use of bioimpedance measurements. A small alternating current is applied to two or more electrodes which are attached to a patient and the corresponding potential drop is measured. The various fluid compartments of a human body contribute differently to the measured signals. The use of multiple frequencies allows the intracellular water (ICV) and extracellular water (ECV) volumes to be determined. An example of such a device is described in the international patent application WO 92/19153. However, this document discloses no method regarding how the dry weight of the particular patient can be derived.

Hence there is a need for a non-invasive, accurate and easy to use method for dry weight assessment. This method would be of major benefit to the management of dialysis patients and could significantly reduce hospitalisation costs in the long term. It is hence an object of this invention to provide such a method.

According to the invention this problem is solved by a method for determining the dry weight $Wgt_{dry}(t)$ of a patient at a time t comprising the steps of determining the extracellular water volume ECV(t) of the patient at the time t, of determining the weight Wgt(t) of the patient at the time t and of deriving the dry weight $Wgt_{dry}(t)$ of the patient from an intersection of a function derived from the determined ECV(t) and Wgt(t) values with a previously established extracellular water volume (ECV) against dry weight ($Wgt_{dry}$) reference relation representing healthy subjects.

The inventive method is based on the observation that by looking at the ECV and the weight of a patient both values should approach the ECV and dry weight values of healthy subjects the longer a patient is being treated by renal replacement therapy, i.e. dialysis. Successive measurements therefore directly pinpoint to the intersection with the previously established ECV against $Wgt_{dry}$ reference relation and thus to the dry weight of the patient being treated. In fact it has turned out that a first estimate can be obtained from a single reading for the ECV(t) and Wgt(t) values by deriving a function, most notably a straight line, which can directly be defined by the ECV(t) and Wgt(t) values. The intersection of this function with the ECV against $Wgt_{dry}$ reference relation for healthy subjects can then easily be calculated and thus the dry weight $Wgt_{dry}(t)$ of the patient be derived.

In a preferred embodiment of the invention ECV(t) is derived by a bioimpedance measurement. The bioimpedance measurement may be a whole body or a segmental measurement.

In an embodiment of the invention which is particularly easy to apply, the intersection of the function derived from the determined ECV(t) and Wgt(t) values with the previously established ECV against $Wgt_{dry}$ reference relation is determined by using the expression $$Wgt_{Dry}(t) = \frac{ECV(t) - \beta_e \cdot Wgt(t)}{\alpha_e - \beta_e}, \qquad (1)$$

wherein $\alpha_e$ and $\beta_e$ are empirically determined coefficients. The coefficient $\alpha_e$ represents the slope of a previously established ECV against $Wgt_{dry}$ reference line, and $\beta_e$ is the slope of a straight line through the Wgt(t)/ECV(t) data pair.

An even more advantageous embodiment of the invention involves the storage of several $ECV(t_i)$ and $Wgt(t_i)$ values at times $t_i$, i=1 ... j, preferably between subsequent dialysis treatments. A more accurate estimate of the dry weight $Wgt_{dry}(t_j)$ is thus derived by a linear regression analysis.

A more refined embodiment of the invention determines a compartmental mass correction $\Delta m(t)$ in order to take into account an individually variable mass of certain body compartments for each patient. This compartmental mass correction $\Delta m(t)$ enables a more accurate comparison with the previously established ECV against $Wgt_{dry}$ reference relation representing healthy subjects which should have been derived from compartmental mass corrected data as well in order to represent some kind of average compartmental mass contribution to the dry body weight $Wgt_{dry}$.

In a preferred embodiment of the invention the dry body weight $Wgt_{dry}(t)$ is derived by employing a correction term to equation (1) which is dependent on $\Delta m(t)$:

$$Wgt_{Dry}(t) = \frac{ECV(t) - \beta_e \cdot Wgt(t)}{\alpha_e - \beta_e} - \frac{\alpha_e \cdot \Delta m(t)}{\beta_e - \alpha_e}. \qquad (2)$$

Examples for compartments which may contribute to $\Delta m(t)$ are fat and muscle tissues. These compartments may vary considerably from one healthy individual to another. If both fat and muscle are considered the compartmental mass correction $\Delta m(t)$ may be decomposed into a fat mass correction $\Delta f(t)$ and a muscle mass correction $\Delta m_{muscle}(t)$ as defined by equation (3):

$$\Delta m(t) = \Delta f(t) + \Delta m_{muscle}(t) \quad (3).$$

It has to be noted, however, that Δm(t) in equation (2) only represents those correction parts of the respective compartments which do not contribute to the ECV(t) value. These compartments add to the weight of a patient, but not to the ECV volume. For the fat mass correction Δf(t) it is a useful approximation that the fat mass has no contribution to the ECV volume, i.e. independent of the fat mass and thus Δf(t) there is no change in ECV. This is however not true for the muscle compartment. Assuming proportionality between the muscle mass $m_{muscle}(t)$ which has no ECV contributions and the volume $ECV_{muscle}(t)$ of extracellular water in the muscle compartment, a proportionality factor $\lambda_{muscle,ECV}$ may be defined according to equation (4):

$$\lambda_{muscle,ECV} = \frac{ECV_{muscle}(t)}{m_{muscle}(t)}. \quad (4)$$

With the aid of equation (4) the muscle mass correction $\Delta m_{muscle}(t)$ in equation (3) can be derived by equation (5):

$$\Delta m_{muscle}(t) = \left(1 - \frac{\lambda_{muscle,ECV}}{\alpha_e}\right) \Delta M_{muscle}(t), \quad (5)$$

where $\Delta M_{muscle}(t)$ is the total mass correction for the muscle compartment, including also the contributions from the ECV volume.

In order to determine the compartmental mass correction Δm(t) either directly or by further refined mass corrections like the fat mass correction Δf(t) and/or the muscle mass correction $\Delta m_{muscle}(t)$ (or $\Delta M_{muscle}(t)$, respectively), another preferred embodiment of the invention makes use of methods and/or further measurements to derive such data.

Such an embodiment may determine the compartmental mass correction with the help of a measurement of the intracellular water volume ICV(t) of the patient at the time t. As indicated above the ICV(t) and ECV(t) values can be determined simultaneously by the same measurement process.

As an example, the fat mass correction Δf(t) may—in a further mode of the invention—be determined from the ICV(t) and ECV(t) values according to equation (6):

$$\Delta f(t) = Wgt(t) - \frac{(1 - \rho_e \cdot \alpha_e - \rho_i \cdot \alpha_i) \cdot ICV(t)}{\alpha_i} - \rho_i \cdot ICV(t) - \rho_e \cdot ECV(t), \quad (6)$$

where $\alpha_i$ is a further empirical coefficient, and $\rho_e$ and $\rho_i$ are the densities of the ECV and the ICV compartments, respectively (≈1 kg/liter).

In fact the fat mass correction Δf(t)—as in the derivation of equation (6) shown below—may very well approximate the total compartmental mass correction Δm(t): If $\Delta M_{muscle}(t)$ does not deviate significantly from the population average $\Delta m_{muscle}(t)$ may be set to zero and thus Δm(t)≈Δf(t). On the other hand it is only the part of $\Delta m_{muscle}(t)$ which has no ECV contributions which enters equation (3). By redefining Δf(t) as simply representing the total of the right hand side of equation (3) it is not even necessary to make the distinction between Δf(t) and $\Delta m_{muscle}(t)$.

Yet another embodiment of the inventive method also makes use of the ICV(t) value. It derives the dry weight $Wgt_{dry}(t)$ of the patient at the time t not only from an intersection of a function derived from the determined ECV(t) and Wgt(t) values with a previously established ECV against $Wgt_{dry}$ reference relation representing healthy subjects, but also from an intersection of a function derived from the determined ICV(t) and Wgt(t) values with a previously established ICV against $Wgt_{dry}$ reference relation representing healthy subjects. In this case the dry weight may be derived with the aid of equation (7):

$$Wgt_{dry}(t) = Wgt(t) - \left(ECV(t) - \frac{ICV(t)\alpha_e}{\alpha_i}\right)\rho_e, \quad (7)$$

where the coefficients have the same meaning as in equation (6).

It is also an object of the invention to provide a device for a non-invasive, accurate and easy to use dry weight assessment. The invention therefore also concerns a device comprising a microprocessor unit which in turn comprises a microprocessor program storage unit, an input unit to enable the values of ECV(t) and Wgt(t) to be entered into the device, and a computer storage unit for storing the ECV(t) and Wgt(t) values, wherein the microprocessor program storage unit comprises a program for deriving the dry weight $Wgt_{dry}(t)$ from an intersection of a function derived from the stored ECV(t) and Wgt(t) values with a previously established ECV against $Wgt_{dry}$ reference relation representing healthy subjects.

In a preferred embodiment of the invention the device further comprises means for determining the ECV(t) value and/or the Wgt(t) value. The means for determining the ECV(t) value may be a bioimpedance device, applied in a whole body or segmental measurement mode.

The input unit may be a manual user interface such as a keyboard in order to enable the input of the ECV(t) and Wgt(t) values. In a particularly convenient embodiment the means for determining the ECV(t) value and/or the means for determining the Wgt(t) value are directly linked to the input unit which contains a corresponding interface in this case. The manual input of these values is then no longer necessary.

In further embodiments of the invention the program in the microprocessor storage unit employs equation (1) or a linear regression analysis as outlined above in order to derive the dry weight $Wgt_{dry}(t)$.

A further improved mode of the device according of the invention makes use of a compartmental mass correction Δm(t) as described in equation (2). For the determination of Δm(t) the device may also comprise means for determining the ICV(t) value, preferably a bioimpedance device which simultanously measures the ECV(t) and ICV(t) values. In this device the input unit also enables entering the ICV(t) value and the computer storage unit is able to store the ICV(t) value. The program for deriving the dry body weight $Wgt_{dry}(t)$ is then determining the compartmental mass correction Δm(t) by using this ICV(t) value. For this purpose equation (6) may be implemented in the program.

In another embodiment of the device according to the invention and also using the ICV(t) value, the program stored in the microprocessor storage unit comprises a program part to derive the dry weight $Wgt_{dry}(t)$ also from an intersection of a function derived from the determined ICV(t) and Wgt(t) values with a previously established ICV against $Wgt_{dry}$ reference relation representing healthy subjects.

Figure 2:
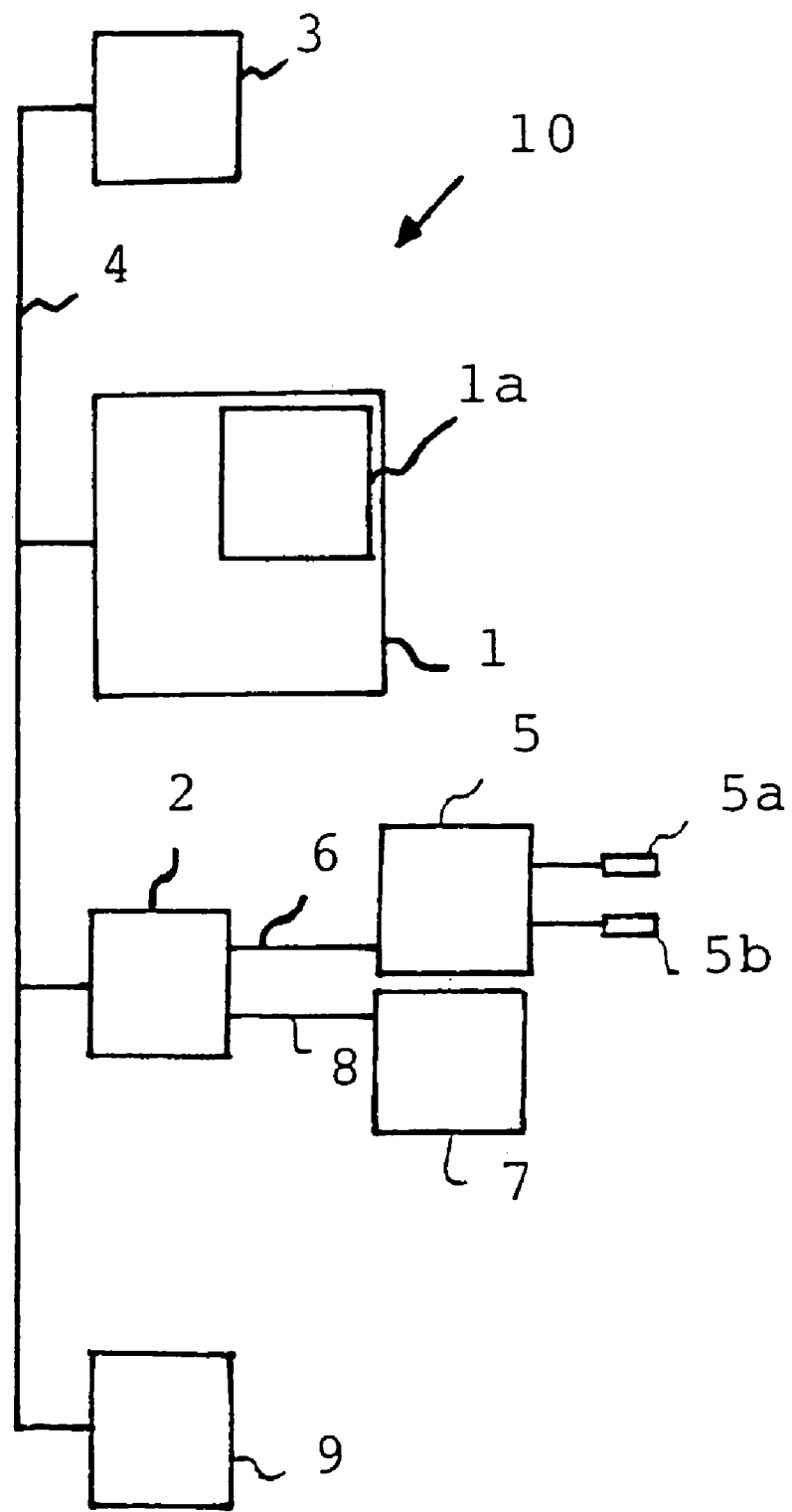
Figure 3A:
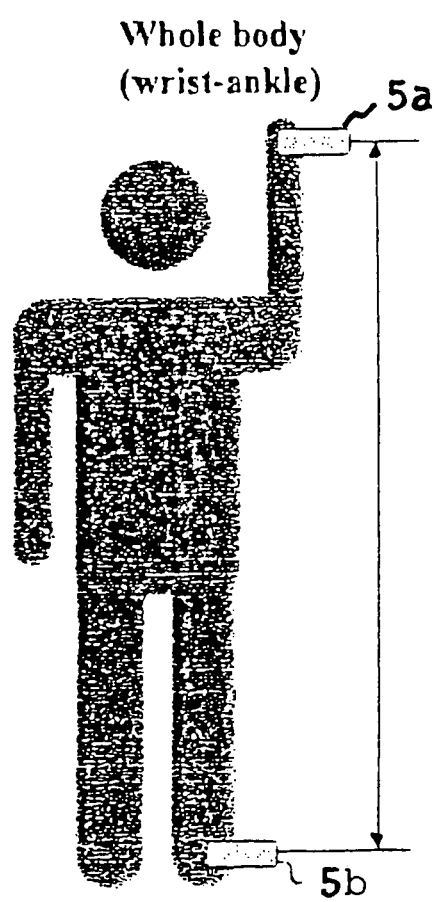
Figure 3B:
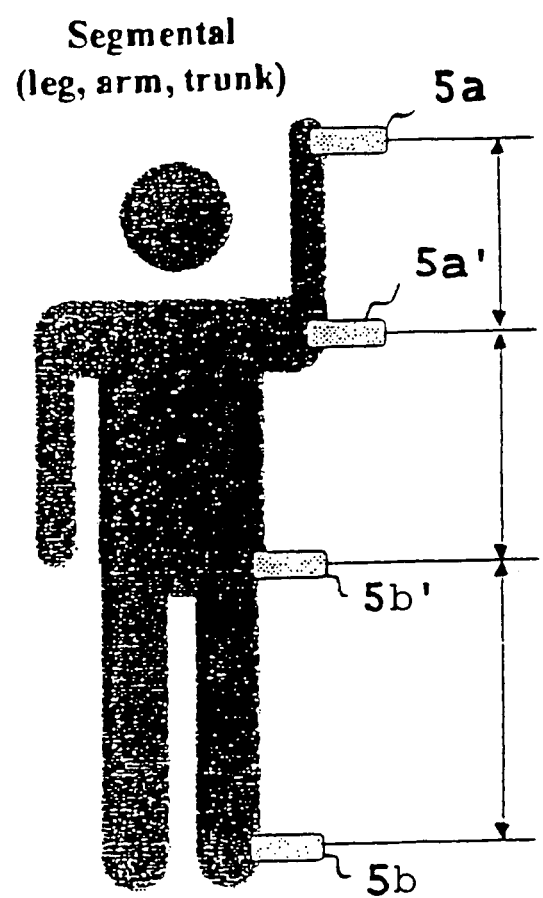
Figure 4:
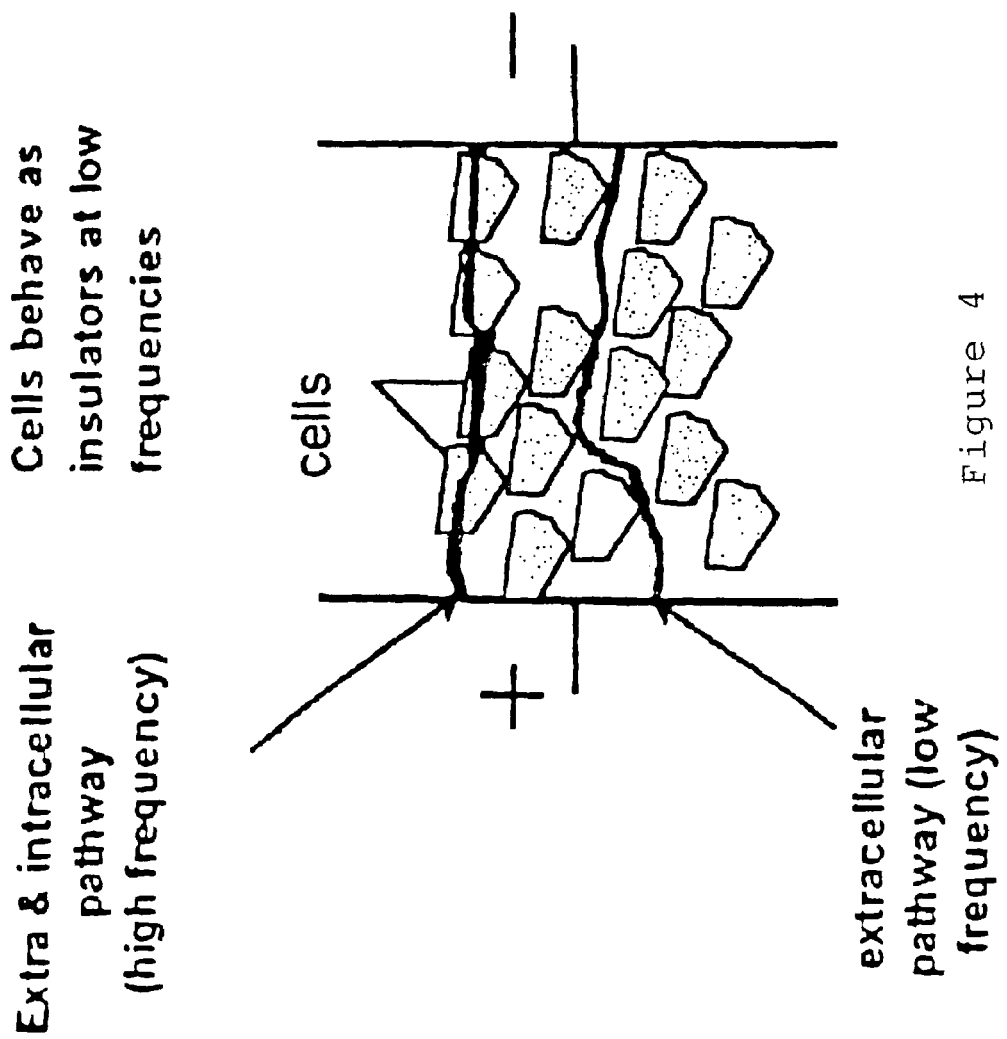
Figure 5A:
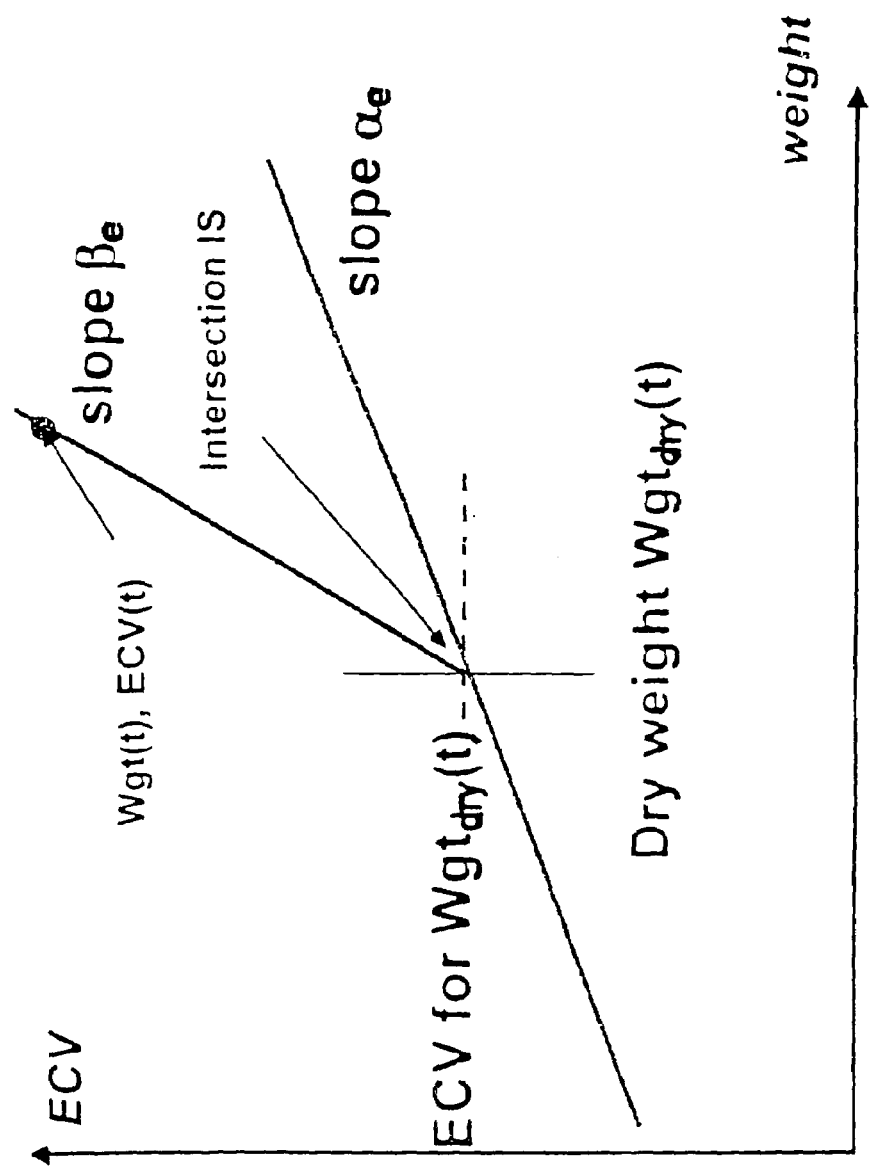
Figure 5B:
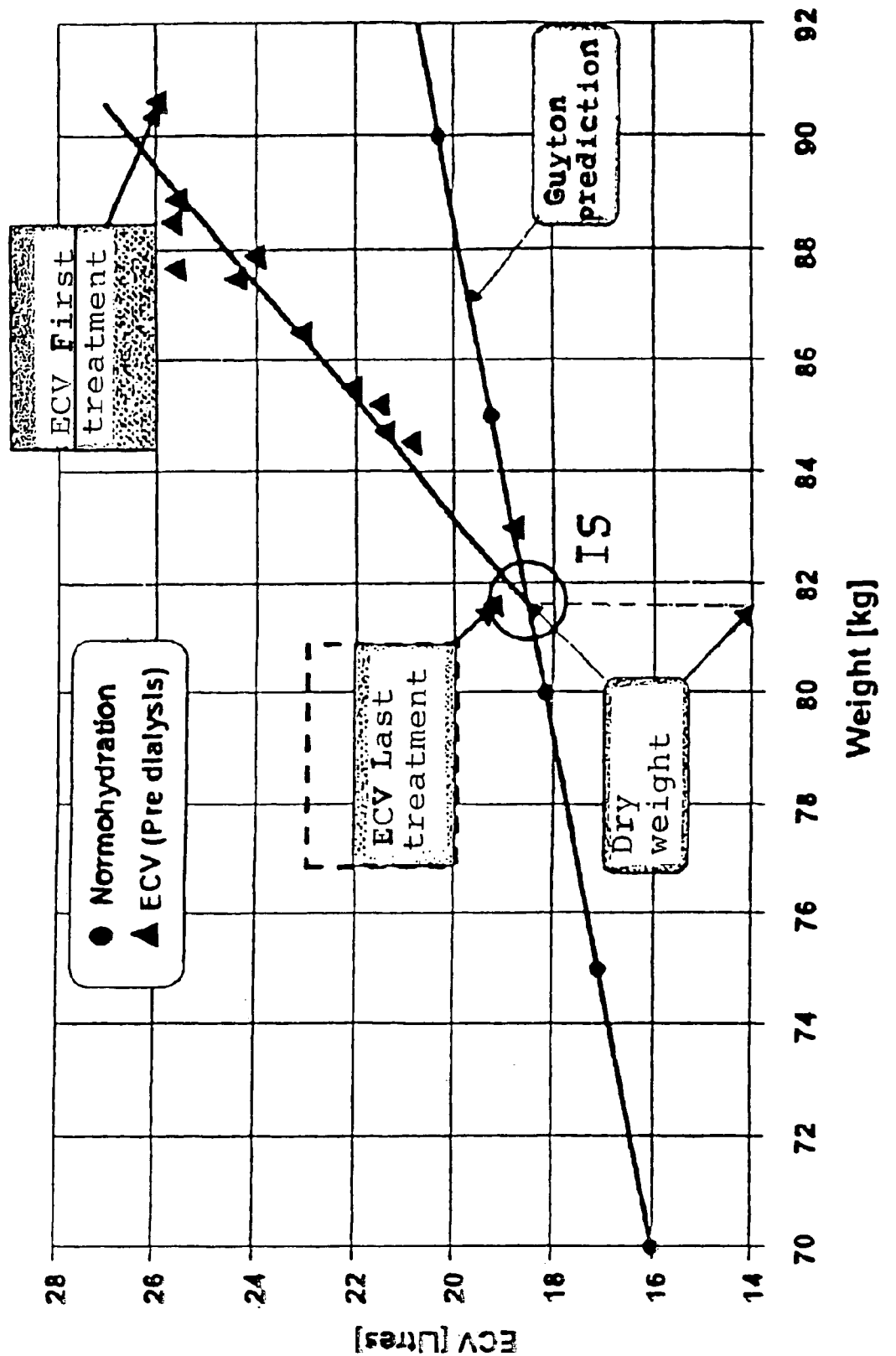
Figure 6:
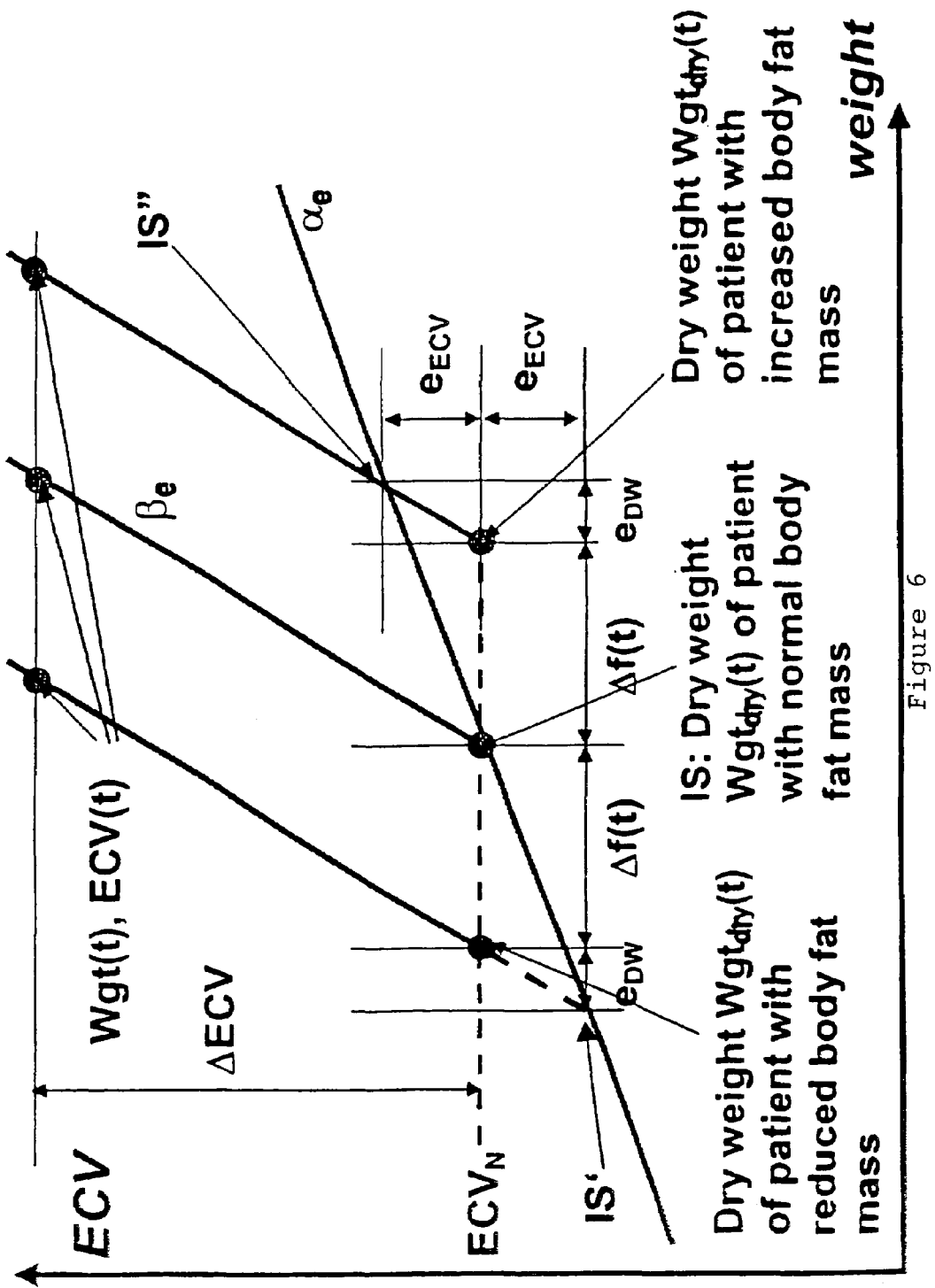
Figure 7:
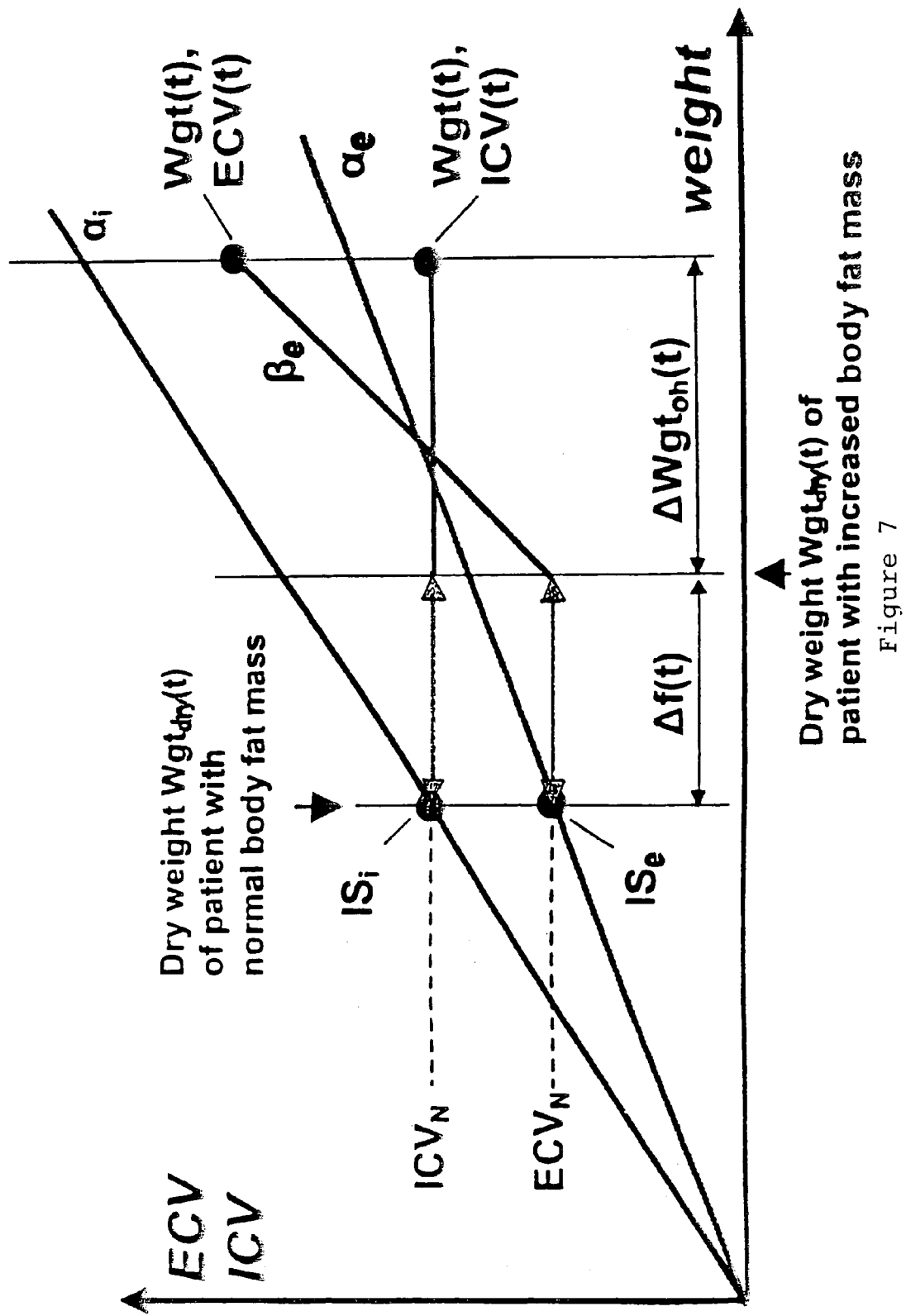

For an improved understanding of the invention non-restrictive examples will be described with reference to the appended drawings in which FIG. 1 shows an illustration of typical body composition ratios of the human body, FIG. 2 schematically shows an embodiment of a device for determining the dry weight of a patient according to the invention, FIG. 3a shows a bioimpedance electrode arrangement for whole body bioimpedance measurements, FIG. 3b shows a bioimpedance electrode arrangement for segmental body bioimpedance measurements, FIG. 4 shows an illustration of a bioimpedance measurement for determining the ECV and/or ICV contributions, FIG. 5a shows an ECV against weight diagram graphically illustrating the finding of the dry weight $Wgt_{dry}(t)$ according to a first embodiment of the method according to the invention, FIG. 5b shows an ECV against weight diagram with subsequent $Wgt(t_i)/ECV(t_i)$ measurements for a dialysis patient (triangles) with a straight line obtained by regression analysis and the corresponding finding of the dry weight $Wgt_{dry}(t)$ according to a second embodiment of the method according to the invention;

FIG. 6 shows an ECV against weight diagram graphically illustrating the influence of a fat mass correction term $\Delta f(t)$ for a third embodiment of the method according to the invention, and FIG. 7 shows an ECV against weight and an ICV against weight diagram graphically illustrating a fourth embodiment of the method according to the invention which also takes a fat mass correction $\Delta f(t)$ into account.

The composition of the human body can be described by a number of compartments which may be expressed as typical fractions of the total body weight as indicated in FIG. 1. In patients with kidney failure the ECV becomes expanded due to the ingestion of water. Other compartments are thought to be largely unaffected by changes in a patient's fluid status. Consequently measurement of the ECV is clearly a useful parameter which could help with dry weight management.

In order to support normal homeostasis a minimum ECV must be required for a given weight. Hence to a good approximation ECV is linearly proportional to weight and may be determined via prediction formulae. According to Guyton physiology (A. C. Guyton: Textbook of Medical Physiology, W.B. Saunders Company, 1991) there is approximately 15 liters of ECV for a weight of 70 kg for a healthy subject with normal fluid and nutrition status. New investigations on healthy subjects revealed the following reference relation between measured ECV and measured $Wgt_{dry}$:

$$ECV = \alpha_e \cdot Wgt_{dry} \qquad (8),$$

with $\alpha_e=0,214$ liters/kg for females and and $\alpha_e=0,239$ liters/kg for males. The value for $\alpha_e$ expressed as a ratio is 14,98/70 and 16,73/70. This is very close to the relationship given by Guyton physiology.

The invention is based on the observation that dialysis patients have an expanded ECV and that therefore the measured ECV must be higher for a given weight than for healthy subjects. If the weight of a fluid overloaded dialysis patient is reduced over many treatments by removal of fluid then the measured ECV should fall, too. Eventually the ECV of the dialysis patient should converge to or close to that of a healthy subject with no renal failure.

An embodiment of a device for determining the dry weight $Wgt_{dry}$ of a patient according to the invention is shown in FIG. 2. The device 10 comprises a microprocessor unit 1 which in turn comprises a microprocessor program storage unit 1a. By means of a link 4 the microprocessor unit 1 is connected to an input unit 2 and a computer storage unit 3. A program for deriving the dry weight $Wgt_{dry}(t)$ of a patient at a time t is stored in the microprocessor program storage unit 1a.

In a first embodiment the microprocessor program derives the dry weight $Wgt_{dry}(t)$ as follows according to the invention: The extracellular water volume ECV(t) of the patient at the time t is determined and entered into the input unit 2 which passes the value to the computer storage unit 3 where it is stored.

The weight Wgt(t) of the patient at the time t is also determined and processed similarly. The program for deriving the dry weight $Wgt_{dry}(t)$ is capable of calculating an intersection between a function derived from the stored ECV(t) and Wgt(t) values and the previously established ECV against $Wgt_{dry}$ reference line representing healthy subjects according to equation (8). The function derived from the stored ECV(t) and Wgt(t) values reflects the fact that these values can only change in a particular manner in the predicted progress of dialysis therapy.

To determine the ECV(t) value means 5 are provided which are connected to the input unit 2 by a link 6. The means 5 is a bioimpedance measurement device. For the bioimpedance measurement various electrode arrangements are possible. In FIG. 2 only two electrode elements 5a and 5b are attached to the bioimpedance measurement device 5. Each of the electrode units 5a and 5b consists of a current injection electrode and a potential pick up electrode (not shown). By applying the two electrode units 5a and 5b to the wrist and the ankle of a patient, respectively, as outlined in FIG. 3a, the whole body impedance may be determined. Under this electrode configuration the body is assumed to be a homogenous cylinder. However by use of electrodes on limbs, segmental sections of the body may be isolated allowing localised volume measurements. This has the advantage that localised volume measurements are possible and an improved accuracy in the determination of the whole body fluid status may be achieved. Such a configuration is displayed in FIG. 3b. Additional electrode units 5a' and 5b' are attached close to the corresponding shoulder and the hip of the patient enabling a segmental approach to the body elements leg, arm and trunk.

The ECV(t) value is determined by exploiting the fact that the electrical impedance of body tissue changes as currents of different alternating frequencies are applied to the patient via the electrodes. At low frequencies the cells behave as insulators and the applied current passes only through the ECV spaces. At high frequencies the cells become conductive and thus current passes through both the ICV and ECV spaces. This is illustrated in FIG. 4. Measurement of the impedance over at least two frequencies, better over a range of frequencies, allows an impedance locus to be constructed from which the resistance of the ICV and ECV components may be determined. Hence the volumes of the respective compartments can then be calculated from the resistance information, based on compartment resistivity constants available from prior studies for which the volumes were also determined by dilution measurements.

A bioimpedance device performing such calculations is distributed by Xitron Technologies under the trademark Hydra™. Details about this device are disclosed in the international patent application WO 92/19153.

An advantage of a first mode of the invention is that only ECV values need to be determined. Therefore only measurements at frequencies being low enough are necessary which have negligible contributions from the ICV compartment. Due to this fact the ECV values can be determined much more accurately than the ICV values for which frequencies are necessary which always lead to contributions from both compartments.

Other methods proposed in the art address the fluid status of a patient by involving the ICV compartment as well, like analyzing ratios of the kind ECV/(ECV+ICV) or ECV/ICV. Since there is always a discussion how well the impedance locus represents the different compartments such approaches inherently contain deficiencies which are avoided by the claimed invention as no simultaneous analysis of the two compartments remains necessary. (In fact the ICV value may instead be used for a second order correction as will be described below.)

Returning to the embodiment shown in FIG. 2, means 7 are also provided for determining the weight Wgt(t) of the patient which are connected to the input unit 2 by a link 8. The means 7 consist of a scales device which are well known in the art.

In the embodiment shown in FIG. 2 the input unit 2 contains an interface by which the values for ECV(t) and Wgt(t) are directly transfered via the link 4 to the computer storage unit 3. It may also be possible that the determined values for ECV(t) and Wgt(t) are manually entered into the input unit 2 by a user.

A first procedure according to which the program stored in the microprocessor program storage unit 1a derives the dry weight $Wgt_{dry}(t)$ is illustrated in FIG. 5a: In this figure the reference relation between the ECV and $Wgt_{dry}$ for healthy subjects is given as a straight line with slope $\alpha_e$ according to equation (8). A single Wgt(t) and ECV(t) measurement of a dialysis patient is denoted by the offline circle. The program for deriving the dry weight $Wgt_{dry}(t)$ of the dialysis patient is now using equation (1) to derive $Wgt_{dry}(t)$. This equation represents the calculation of the intersection IS of a line through the Wgt(t)/ECV(t) data point with the reference line. This line has the slope $\beta_e$. This slope is expected to be close to $1/\rho_e$, i.e. in a first estimate the program uses $\beta_e=1$ liter/kg. The weight coordinate of the intersection directly gives the sought $Wgt_{dry}(t)$ value.

FIG. 5b shows the ECV(t) and Wgt(t) values for a single patient between several subsequent dialysis treatments (triangles), the measurements being made directly before the beginning of a dialysis treatment (pre-dialysis). By successive reduction in post dialysis weight the Wgt(t)/ECV(t) measurement pairs shift increasingly closer to the values predicted for a healthy subject indicating a progressive improvement in the fluid status of the patient. To improve the accuracy of the calculated $Wgt_{dry}(t)$ value, a straight line may be fitted to the Wgt(t)/ECV(t) measurement pairs by linear regression analysis according to a second embodiment. In fact these straight lines turned out to have a slope of approximately 1 liter/1 kg, suggesting that most of the excess fluid accumulated and hence weight gain is really sequestered in the ECV compartment. As in the case of a single measurement pair the intersection IS of the straight line with the ECV against $Wgt_{dry}$ reference for healthy subjects directly identifies the dry weight $Wgt_{dry}(t)$ of the patient. In FIG. 5b one obtains a value of $Wgt_{dry}(t)=81.6$ kg using this method.

The computer storage unit 3 of the device 10 is hence also able to store $Wgt(t_i)/ECV(t_i)$ data pairs for various times $t_i$, which are preferably be aquired directly before subsequent dialysis treatments i=1 . . . j, as represented by the measurements shown in FIG. 5b. The program for deriving the dry weight $Wgt_{dry}(t_j)$ at the latest time $t_j$ is then able to retrieve all $Wgt(t_i)/ECV(t_i)$ data pairs from the computer storage unit 3. Depending on the scatter of the data the program performs a linear regression analysis either with the constraint that the slope $\beta_e$ has a fixed value (e.g. $\beta_e=1$ liter/kg) or not, or both to offer the user the results of both calculations. Taking an arbitrary Wgt/ECV data pair on the derived straight line function for ECV(t) and Wgt(t) in equation (1), the dry weight $Wgt_{dry}(t_j)$ is determined with the help of equation (1) as well. Further statistical information (e.g., correlation coefficients etc.) as is known in the art of regression analysis may be provided in addition.

In order to further improve the accuracy of the derived dry weight $Wgt_{dry}(t)$ the program stored in the microprocessor program storage unit 1a has—in a third embodiment—a further section which takes a compartmental mass correction $\Delta m(t)$ into account which accounts for individual variations of the dry weight in certain compartments like the fat and/or muscle compartment of a human being. The dry weight $Wgt_{dry}(t)$ is then calculated according to equation (2).

The influence of the mass correction $\Delta m(t)$ in terms of the fat mass correction $\Delta f(t)$ is illustrated by FIG. 1: Apart from the ECV and ICV contributions to the total body weight the next most important contribution is attributed to fat mass. Other compartments are an order of magnitude less relevant. For the sake of simplicity, all remaining body mass which is neither ECV nor ICV may be regarded as, "the fat mass compartment". The fat mass correction $\Delta f(t)$ originates from this compartment. (It may also be possible to consider other compartments like muscle mass explicitly as outlined by equation (3).)

It is this particular "average" fat compartment which may vary considerably from subject to subject, for healthy subjects as well as for dialysis patients. This variation will lead to some error in the $Wgt_{dry}(t)$ data if it is not considered. In fact the reference line according to equation (8) has been established by normalizing the weight data in healthy subjects by taking $\Delta f$ into account.

Refering to FIG. 6 the impact of $\Delta f(t)$ becomes apparent: Taking the reference line of healthy subjects with slope $\alpha_e$ and the middle line of the three lines with slope $\beta_e$, one would have the same situation as in FIG. 5a. In case the dialysis patient does not have a, "normal body fat mass", the weight Wgt(t) of the patient is shifted to the left or to the right by the fat mass correction $\Delta f(t)$, depending on whether the patient has a reduced or an increased body fat mass, respectively. In the latter two cases the intersections IS' and IS" would lead to an inaccurate dry weight $Wgt_{dry}(t)$ value. Instead the dry weight $Wgt_{dry}(t)$ is given by the weight values of the respective circled data points, i.e. an amount $e_{DW}$ has to be added or subtracted from the calculated intersection weight value. This amount $e_{DW}$ is given by the second term in equation (2), by which equation (2) differs from the simplified equation (1).

As is also apparent from FIG. 6 the fat mass correction $\Delta f(t)$ is considered by equation (2) as a contribution which adds to the weight Wgt(t), but not to the ECV(t) value. In case compartmental corrections are explicitly considered which have contributions from the ECV volume, only those parts contribute to the compartmental mass correction Δm(t) which have no contributions from the ECV volume.

In order to derive the fat mass correction Δf(t) itself, the program may make use of equation (6). For this purpose the means 5 for determining the ECV(t) value is also a means for determining the ICV(t) value. As has been outlined above there are devices available on the market which measure both values simultanously.

Equation (6) is based on the following relations: A relation similar to equation (8) can be defined between the ICV and $Wgt_{dry}$ for healthy subjects, i.e.

$$ICV = \alpha_i \cdot Wgt_{dry} \quad (9).$$

A survey has revealed the following values of the coefficients: $\alpha_i = 0{,}253$ liters/kg for females and $\alpha = 0{,}333$ liters/kg for males.

The values—as in the determination of the values of the coefficents of equation (8)—have been found in an optimization strategy to fit measured weights of healthy subject to a sum of the ECV, the ICV and the fat mass compartments. The latter is in turn divided into an average fat mass and an individual fat mass correction Δf compartment. The fat mass correction Δf was the only free parameter for a given measured total weight during the optimization calculation which took into account the individuality of the various healthy subjects.

Furthermore its has been revealed in this study that the ICV volumes do not significantly differ from treatment to treatment for a dialysis patient. In case the patient is neither catabolic or anabolic this volume should even be identical to the ICV volumes of heathly subjects. After having established the coefficients of equation (9) it is therefore possible to devide the total body mass of a dialysis patient into the ICV part which can be determined by the measured ICV(t) value multiplied by the corresponding density $\rho_i$, into the ECV part which can be determined by the measured ECV(t) value multiplied by the corresponding density $\rho_e$ and which is the sum of a part $ECV_N$ representing the healthy value and a deviation $\Delta ECV$ which accounts for the disturbed fluid balance in a dialysis patient (see FIG. 6), the average fat mass contribution and, last not least, the fat mass correction Δf(t). The average fat mass contribution is not a free parameter in the calculation as it can be expressed as dry body weight of average and healthy subjects minus the ICV and ECV contributions of these subjects. The dry body weight of healthy and average subjects is then substituted by equation (9). As a result equation (6) is found where Δf(t) remains the only unknown parameter.

For the densities $\rho_e$ and $\rho_i$ the program uses 1 kg/liter as these compartments basically consist of water.

Patients who just start dialysis therapy show ICV volumes that are slightly increased compared with the rather steady values found after some dialysis treatments. The outlined procedure to determine the fat mass correction Δf(t) is however still a good approximation even in this case.

In a fourth embodiment the dry weight $Wgt_{dry}(t)$ of a patient is derived not only from an intersection of a function derived from the determined ECV(t) and Wgt(t) values with a previously established ECV against $Wgt_{dry}$ reference relation representing healthy subjects, but also from an intersection of a function derived from the determined ICV(t) and Wgt(t) values and a previously established ICV against $Wgt_{dry}$ reference relation representing healthy subjects.

The method which is used by the program stored in the microprocessor program storage unit 1a to derive the dry weight $Wgt_{dry}(t)$ according to the fourth embodiment is illustrated in FIG. 7 where both a previously established ECV against $Wgt_{dry}$ reference relation and a previously established ICV against $Wgt_{dry}$ reference relation representing healthy subjects are shown. The shown relations simply correspond to equations (8) and (9), i.e. they are given by straight lines with slopes $\alpha_e$ and $\alpha_i$, respectively.

This embodiment takes advantage of the fact any compartmental mass correction αm(t) for patients deviating from normal dry weight will cause a horizontal shift on the x-axis which is identical for both reference relations. Assuming further—as an preferred mode—that the compartmental mass correction Δm(t) is set equal to a fat mass correction Δf(t) which in turn neither has any ECV or ICV contributions, the compartmental mass correction Δm(t) is solely represented by a horizontal shift with no vertical shift—similarly as shown in FIG. 6.

The weight thus obtained is the target dry weight $Wgt_{dry}(t)$ for this individual patient. Due to overhydration the measured weight Wgt(t) will be larger than $Wgt_{dry}(t)$. The difference of the two parameters, the overhydration weight $\Delta Wgt_{oh}(t)$, may again be represented by functions connecting the $ECV_N/Wgt_{dry}(t)$ and $ICV_N/Wgt_{dry}(t)$ data points, respectively, with the measured ECV(t)/Wgt(t) and ICV(t)/Wgt(t) data points, respectively. In the mode shown in FIG. 7 these function are taken as straight lines with slopes $\beta_e$ and $\beta_i$. Similar to the derivation of equation (1) $\beta_i$ is set to 0 liters/kg.

The program stored in the microprocessor storage unit 1a makes now use of equation (7) which is derived from the above mentioned fact that the shifted functions accounting for the overhydration weight $\Delta Wgt_{oh}(t)$ in the ECV against weight and ICV against weight diagrams have to be shifted by the same amount Δf(t) horizontally to intersect with the corresponding reference relations for healthy subjects, i.e. at the intersections $IS_e$ and $IS_i$.

Independent of whether a fat mass correction Δf(t) is taken into account or not and which embodiment of a method to derive the dry weight $Wgt_{dry}(t)$ is implemented in the microprocessor program, the result for $Wgt_{dry}(t)$ is finally passed on to an output unit 9 which is a display device and which displays the result to a user. Further intermediate results like the measurement values or the fat mass correction Δf(t) might add to the informative character of the display.

The disclosed device and method according to the invention is hence able to provide for a powerful technique for the management of dry weight. It is obvious that the scope of the claimed invention is not limited to the equation (8) as far as the previously established ECV against $Wgt_{dry}$ reference relation for healthy subjects is concerned. Any other established relation can be used instead.

Management of any patient is possible, independent of the treatment modality, i.e. the invention is applicable for hemodialysis, hemofiltration, hemodiafiltration or any forms of peritoneal dialysis (all these treatment modalities are summarized throughout this patent application by the terminology "a dialysis treatment"). Furthermore, measurement in virtually any setting would be practical including the home, clinic, dialysis unit, ward or intensive care environment.

The invention claimed is:

1. A method for determining the dry weight $Wgt_{dry}(t)$ of a patient at a time t comprising the steps of:
   determining the extracellular water volume ECV(t) of the patient at the time t,
   determining the weight Wgt(t) of the patient at the time t,
   deriving the dry weight $Wgt_{dry}(t)$ of the patient from an intersection of a function derived from the determined ECV(t) and Wgt(t) values with a previously established extracellular water volume (ECV) against dry weight ($Wgt_{dry}$) reference relation representing healthy subjects.

2. The method according to claim 1 characterized in that ECV(t) is derived from a bioimpedance measurement.

3. The method according to claim 2 characterized in that the bioimpedance measurement is a whole body measurement.

4. The method according to claim 2 characterized in that the bioimpedance measurement is a segmental measurement.

5. The method according to claim 1 characterized in that $Wgt_{dry}(t)$ is determined using the following expression:

$$Wgt_{Dry}(t) = \frac{ECV(t) - \beta_e \cdot Wgt(t)}{A_e - \beta_e},$$

where $\alpha_e$ and $\beta_e$ are empirically determined coefficients.

6. The method according to claim 1 characterized in that the $ECV(t_i)$ and $Wqt(t_i)$ values of a patient at times $t_j$, i=1 . . . j are stored and that the dry body weight $Wgt_{dry}(t_i)$ is derived by a linear regression analysis.

7. The method according claim 1 characterized in that a compartmental mass correction $\Delta m(t)$ is determined in order to derive the dry body weight $Wgt_{dry}(t)$ from the determined weight Wgt(t).

8. The method according to claim 7 characterized in that the dry weight $Wgt_{dry}(t)$ is derived by the following expression:

$$Wgt_{Dry}(t) = \frac{ECV(t) - \beta_e \cdot Wgt(t)}{\alpha_e - \beta_e} - \frac{\alpha_e \cdot \Delta m(t)}{\beta_e - \alpha_e},$$

where $\alpha_e$ and $\beta_e$ are empirically determined coefficients.

9. The method according to claim 7 characterized in that the compartmental mass correction $\Delta m(t)$ encompasses a fat mass correction $\Delta f(t)$ and/or a muscle mass correction $\Delta m_{muscle}(t)$.

10. The method according to claim 7 characterized in that the intracellular water volume ICV(t) is determined for the patient at the time t and that the determined ICV(t) is used to derive the compartmental mass correction $\Delta m(t)$.

11. The method according to claim 1 characterized in that the method for determining the dry weight $Wgt_{dry}(t)$ of a patient at a time t further comprises the steps of determining the intracellular water volume ICV(t) of the patient at the time t and of deriving the dry weight $Wgt_{dry}(t)$ of the patient also from an intersection of a function derived from the determined ICV(t) and Wgt(t) values with a previously established intracellular water volume (ICV) against $Wgt_{dry}$ reference relation representing healthy subjects.

12. A device (10) for carrying out the method according to claim 1 comprising
 a microprocesaor unit (1) which in turn comprises a microprocessor program storage unit (1a),
 a input unit (2) to enable entering the values of EVC(t) and Wgt(t),
 a computer storage unit (3) for storing the ECV(t) and Wgt(t) value.

13. The device according to claim 12 characterized in that it further comprises means (5) for determining the ECV(t) value.

14. The device according to claim 12 characterized in that it further comprises means (7) for determining the Wgt(t) value.

15. The device according to claim 13 characterized in that the means (5) for determining the ECV(t) value is a bioimpedance measurement device.

16. The device according to claim 12 characterized in that the input unit (2) is a manual user interface.

17. The device according to claim 12 characterized in that the input unit (2) comprises an interface to the means (5) for determining the ECV(t) value and/or the means (7) for determining the Wgt(t) value.

18. The device according to claim 12 characterized in that the program for deriving the dry body wetght $Wgt_{dry}(t)$ uses the following expression:

$$Wgt_{Dry}(t) = \frac{ECV(t) - \beta_e \cdot Wgt(t)}{A_e - \beta_e},$$

where $\alpha_e$ and $\beta_e$ are empirically determined coefficients.

19. The device according to claim 12 characterized in that the computer storage unit (3) is capable of storing the $ECV(t_i)$ and $Wgt(t_i)$ values of a patient at times $t_i$, i=1 . . . j, and that the program for deriving the dry weight $Wgt_{dry}(t_j)$ uses a linear regression analysis.

20. The device according to claim 12 further comprising an output unit (9) that is linked to the microprocessor unit for outputting.

21. The device according to claim 12 characterized in that the program stored in the microprocessor program storage unit (1a) is suitable to determine a compartmental mass correction $\Delta m(t)$ in order to derive the dry body weight $Wgt_{dry}(t)$ from the determined weight Wgt(t).

22. The device according to claim 21 characterized in that the program for deriving the dry body weight $Wgt_{dry}(t)$ uses the following expression:

$$Wgt_{Dry}(t) = \frac{ECV(t) - \beta_e \cdot Wgt(t)}{\alpha_e - \beta_e} - \frac{\alpha_e \cdot \Delta m(t)}{\beta_e - \alpha_e},$$

where $\alpha_e$, and $\beta_e$ are empirically determined coefficients.

23. The device according to claim 21 characterized in that the input unit (2) is also suitable to enable entering a value for the intracellular water volume ICV(t) of the patient at the time t, the computer storage unit (3) is able to store the ICV(t) value and that the program for deriving the dry body weight $Wgt_{dry}(t)$ uses the ICV(t) value in order to determine the mass correction $\Delta m(t)$.

24. The device according to claims 23 characterized in that the device further comprises means for determining the ICV(t) value.

25. The device according to claim 12 characterized in that input unit (2) is also suitable to enable entering a value for the intracellular waler volume ICV(t) of the patient at the time t, the computer storage unit (3) is able to store the ICV(t) value and that the program for deriving the dry weight $Wgt_{dry}(t)$ of a patient at a time t further comprises a part to derive the dry weight $Wgt_{dry}(t)$ also from an intersection of a function derived from the determined ICV(t) and Wgt(t) values
 with a previously established intraceltular water volume (ICV) against $Wgt_{dry}$ reference relation representing healthy subjects.

* * * * *